United States Patent [19]

Fujiwara et al.

[11] 4,329,591
[45] May 11, 1982

[54] METHOD FOR DETECTING SAMPLES

[75] Inventors: Toshihide Fujiwara, Fuchu; Nobutaka Kaneko, Hachiouji, both of Japan

[73] Assignee: Olympus Optical Co., Ltd., Tokyo, Japan

[21] Appl. No.: 155,384

[22] Filed: Jun. 2, 1980

[30] Foreign Application Priority Data

Jun. 8, 1979 [JP] Japan ................................ 54-72074

[51] Int. Cl.³ ........................................... G01N 21/86
[52] U.S. Cl. .................................... 250/548; 356/400; 356/444
[58] Field of Search ............... 250/560, 561, 573, 574, 250/576, 548, 557; 356/244, 432, 433, 444, 440, 443, 400

[56] References Cited

U.S. PATENT DOCUMENTS 3,994,593  11/1976  Kato et al. ......................... 356/444
4,067,760  1/1978  Nelson ............................... 250/548

*Primary Examiner*—David C. Nelms
*Attorney, Agent, or Firm*—Cushman, Darby & Cushman

[57] ABSTRACT

A method for detecting samples by comparing outputs corresponding to a carrier portion free from sample with those corresponding to a carrier portion onto which a sample is applied while detecting said outputs with a plural number of sample detectors arranged in the direction perpendicular to the shifting direction of a carrier, selecting a sample detector showing the highest output reduction ratio as the one to be utilized for sample detection and detecting the end edge of a sample as a time at which output of said sample detector changes from a level darker than a preset value to another level brighter than said preset value.

2 Claims, 13 Drawing Figures

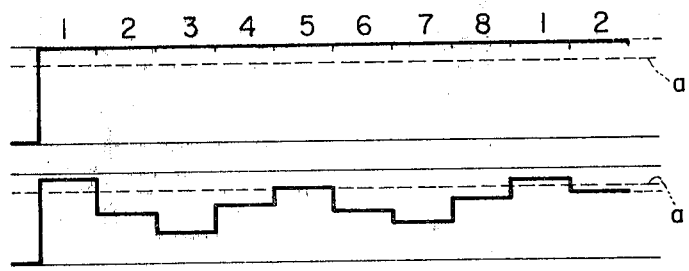
FIG. 5A
FIG. 5B
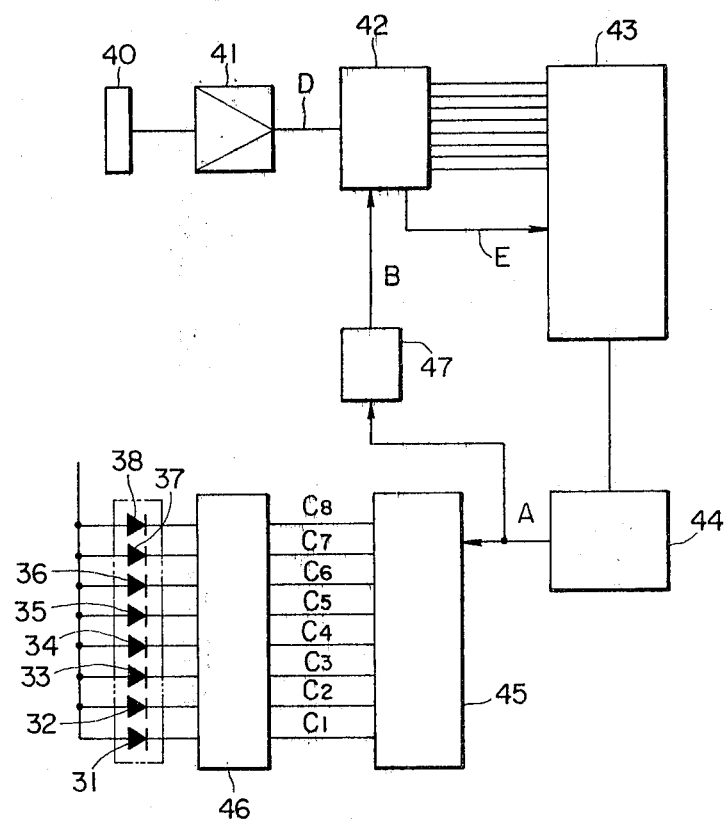
FIG. 6

METHOD FOR DETECTING SAMPLES

BACKGROUND OF THE INVENTION (a) Field of the Invention

The present invention relates to a method for detecting positions of samples applied onto a carrier being shifted in a definite direction, and more specifically to a sample detection method used for quantitative analyses of fractionated patterns of sera in the electrophoresis.

(b) Description of the Prior Art

In the electrophoresis, samples (sera) are applied onto a carrier made of cellurose acetate or the similar material and fractionated patterns of the samples are formed by electrically energizing the carrier. Then, the carrier is colored, discolored and made transparent, whereafter the fractionated patterns are subjected to quantitative analyses with a colorimeter. For automatic analyses of the samples with a colorimeter, the carrier is shifted between a light source and a photo detector, the carrier is stopped each time a sample applied onto the carrier is located right between the light source and photo detector, and the light source and photo detector are moved together in the direction perpendicular to the shifting direction of the carrier to scan the sample for carrying out photometry. Such a photometric apparatus requires a sample detector which precisely detects position of a sample on the carrier when it is located right between the light source and photo detector.

Recently, there has been developed an automatic electrophoretic apparatus so adapted as to carry out all the steps from application of samples onto a carrier to densitometry in electrophoresis. In this electrophoretic apparatus, samples are applied onto a carrier at constant intervals in the step of sample application. However, intervals between the samples are made different at the step of densitometry due to conditions at the intermediate steps, for example, difference in electrophoretic conditions and contraction of the carrier at the drying step. Though such variations in sample intervals are on the order of 2 mm, it is necessary to compensate the variations for carrying out densitometry correctly at the center of the fractionated patterns. Influence due to positional deviations will be more remarkable especially for samples applied onto later portions of the carrier.

In order to meet the requirements described above, there has recently been developed a sample detector having the construction illustrated in FIG. 1 wherein the reference numeral 1 represents a carrier on which electrophoretic patterns of samples are formed and which is shifted in the direction indicated by the arrow. The reference numeral 10 designates a first optical fiber group consisting of optical fibers 11 through 18 (eight optical fibers are shown as a non-limitative example) which have ends 11a through 18a so arranged as to make the lights emerging therefrom incident perpendicularly on the surface of the carrier and arranged in a row in the direction (x direction) perpendicular to the shifting direction of the carrier. At the other ends 11b through 18b of the optical fibers, there are arranged light emitting diodes 31 through 38 so as to correspond to the individual optical fibers. The reference numeral 20 denotes a second optical fiber group consisting of optical fibers 21 through 28 in the same number as those of the first optical fiber group. The individual optical fibers of the second optical fiber group have ends 21a through 28a which are arranged in a row opposite respectively to the ends 11a through 18a of the individual optical fibers of the first optical fiber group so as to receive the lights emerging therefrom. The other ends 21b through 28b of the individual optical fibers of the second optical fiber group are fastened in the form of a bundle. The reference numeral 40 represents a photo detector element arranged in the vicinity of the ends 21b through 28b of the bundled optical fibers, and the reference numeral 41 designates a preamplifier. The reference numeral 3 denotes a light source assembly consisting of a light source lamp 4, a lens system 5, a filter 6, a slit plate 7 and so on, and the reference numeral 8 represents a photo detector which composes a photometric system for carrying out photometry while scanning samples applied onto the carrier in the direction perpendicular to the shifting direction of the carrier. The ends 11a through 18a and 21a through 28a arranged in rows opposite to each other of both the above-mentioned optical fiber groups are positioned at a distance equal to a single pitch 1 of sample intervals as measured from the position of the photometric system. When a sample 2 on the carrier is placed at the position of the photometric system, the next sample 2' is therefore placed between the ends 11a through 18a and 21a through 28a of the optical fibers.

In the sample detector having the above-described construction, the carrier is shifted in the direction indicated by the arrow and at the same time the individual light emitting diodes 31 through 38 are glowed consecutively at a high speed at the timing illustrated in FIG. 2. After all the light emitting diodes have been glowed, they are glowed repeatedly in the sequence of 31, 32 through 38. The lights emitted from the light emitting diodes pass through the optical fibers 11 through 18, emerge from the ends 11a through 18a thereof, pass through the carrier, enters the corresponding optical fibers 21 through 28 of the second optical fiber group 20, transmit therethrough, emerge from the exit ends 21b through 28b thereof and are received by the photo detector element 40. Intensities of the received lights correspond to concentration of the sample applied onto the carrier, and the photo detector element provides, upon receiving the lights, outputs as exemplified in FIG. 3. These outputs are totalized by the preamplifier 41 which provides output as shown in FIG. 4. The preamplifier provides a high output when the light passes through a transparent portion of the carrier free from sample and has high intensity, whereas the output is lowered corresponding to concentration of sample when the light passes through a sample applied onto the carrier. Output corresponding to transparent portion free from sample is exemplified in FIG. 5A, whereas one corresponding to a sample is exemplified in FIG. 5B. Now, it is possible to preset a sample detection level as shown in the dashed lines in FIG. 5A and FIG. 5B respectively. Speaking more concretely, it is possible to preset a level a which is lower than all outputs when a sample is not detected and higher than at least one of outputs when a sample is detected. This level a is usable as a criterion for judging presence of a sample. A turning point from a time at which the outputs produced from the lights having passed through all the optical fibers are higher than the level a to another time at which an output produced from a light having passed through any one of the optical fibers is lower than the level a, just corresponds to the moment that a sample is just located between the ends of the optical fibers arranged in rows. Then, the time at which the outputs produced from the lights having passed through all the optical fibers become higher than the level a corresponds to the moment when the sample deviates from between the ends of the optical fibers. It is therefore possible to detect both the front and rear edges of a sample in this way. When presence of a sample is detected as described above, it is possible to stop the carrier to locate the sample correctly at the position of the photometric system in a definite time determined depending on the gaps as measured from the photometric system to the ends of the optical fibers.

In FIGS. 5 and 5B, the outputs are illustrated on an assumption that they are kept constant when a transparent portion free from sample of the carrier is located between the ends of both the optical fiber groups. In actuality, however, the outputs more or less vary due to the facts that intensities of the lights emitted from the individual light emitting diodes are different and that transmittance of the individual optical fibers is more or less different. Therefore, more adequate judgement can be done when outputs corresponding to the individual light emitting diodes are measured by glowing them before detecting samples, correct output levels for the individual optical fibers are stored on the basis of the measured values, and these levels are used as standard levels (corresponding to the level a shown in FIG. 5A and FIG. 5B) for judgement. Such measurements of output levels for the individual optical fibers permit sample detection with higher accuracy since they correct not only variations in intensities of the lights emitted from the individual light emitting diodes and transmittance of the individual optical fibers but to compensate variations of the entire detector system including drift of the electric circuit. Processing of the data obtained with the above-described sample detector is performed according to a computer program. FIG. 6 shows a block diagram of a data processing system for such a purpose, in which image signals subjected to photoelectric conversion by the photo detector element 40 are amplified by a preamplifier 41, whose outputs are converted by an A/D converter unit 42 into digital signals to be fed and stored into a computer 43. The reference numeral 44 represents an oscillator which is operated with an image detection command from the computer 43 and whose outputs are converted by a converter 45 into signals for glowing the individual light emitting diodes consecutively and fed into a driver circuit 46 which functions to glow the individual light emitting diodes 31, 32, ... consecutively at definite time intervals. On the other hand, the outputs from the oscillator are fed also into a one-shot multivibrator, which in turn provides an output as A/D conversion command to the A/D converter unit 42. The A/D converter unit 42 creates an A/D conversion end signal which is fed into the computer 43 for taking the data thereinto at that time. Since the light emitting diodes are glowed consecutively, it is possible to make the individual light emitting diodes correspond to the data in a relationship of 1:1 so as to identify each item of the data corresponding to each of the light emitting diodes.

FIG. 7 shows a time chart clarifying the signals at the respective stages of the block diagram illustrated in FIG. 6. In FIG. 7, the reference symbol (A) represents signals transmitted from the oscillator and the reference symbol (B) designates outputs from the one-shot multivibrator which is triggered at the falling ends of the transmission signals A. The reference symbols $(C_1)$, $(C_2)$ through $(C_8)$ denote driving signals for the light emitting diodes created by the converter using the transmission signals A and to be used for glowing the light emitting diodes. Upon glowing of the light emitting diodes, the lights are received by the photo detector element to produce image signals, which are amplified by the preamplifier to prepare outputs D. It is possible to feed output signals at the glowing timing of the light emitting diodes into the computer by feeding these output data into the computer at the timing determined on the basis of the conversion end signal E created by the A/D converter unit.

When positions of samples are detected with a sample detector having the above-described construction, a sample at a high concentration provides a broad fractionated patterns, i.e., so widened in the shifting direction of the carrier as to be overlapped with these of the adjacent sample applied onto the carrier as illustrated in FIG. 8 and FIG. 9. In FIG. 9, samples $2'a$, $2''a$ and $2'''a$ at concentrations higher than that of sample $2a$ have sample widths gradually broadened. Therefore, sample positions $2b$, $2'b$, $2''b$ and $2'''b$ corresponding to the standard level a for detecting sample position are different from one another. In other words, positions of the samples to be detected are different depending on concentrations of samples, resulting in an undesirable effect. In case of a sample at a very high concentration such as the sample $2'''a$, sample width becomes broad enough to overlap with the neighboring sample $2''''a$ as shown in FIG. 8, thereby making the overlapped area $2c$ at a concentration higher than the standard level (on the side of the dark level) and making it impossible to detect position of the sample. In case of a sample at a low concentration as shown in FIG. 9, in contrast, the area even at the highest concentration in close to the standard level, thereby making sample detection unstable.

SUMMARY OF THE INVENTION

A general object of the present invention is to provide a method for detecting positions of samples always with high accuracy by arranging a plural number of detectors in the direction perpendicular to the shifting direction of the carrier, selecting a detector which detects the largest difference between bright level and dark level out of the values detected by said detectors and presetting an adequate value matched with the sample concentration detected with the selected detector.

BRIEF DESCRIPTION OF THE DRAWINGS

FIG. 5A shows a chart illustrating an output corresponding to a portion free from a sample of the carrier provided from the sample detector shown in FIG. 1;

FIG. 5B shows a chart illustrating outputs corresponding to a sample portion of the carrier provided by said sample detector;

FIG. 6 shows a block diagram illustrating a circuit for processing data provided from said sample detector;

DESCRIPTION OF THE PREFERRED EMBODIMENT

Figure 10A:
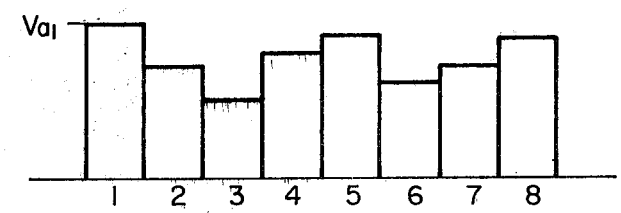
FIG. 10A and FIG. 10B show diagrams descriptive of the method for selecting a sample detector by the method according to the present invention and the method for presetting a standard level.
Figure 10B:
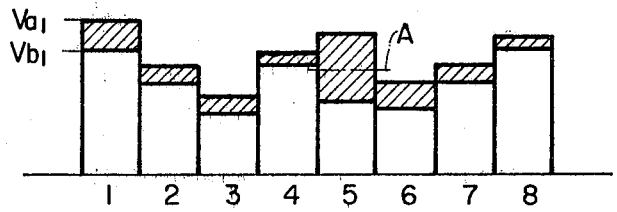

Now, the method for detecting samples according to the present invention will be described more detailedly with reference to a preferred embodiment of the present invention. A carrier is shifted in a sample detector having the same construction as that shown in FIG. 1. The shifting of the carrier is stopped when a first sample 2 applied onto the carrier reaches the position of the photometric system consisting of the light source assembly 3 and the photo detector 8. That is to say, since the space from the leading edge of the carrier to the first sample is constant, the carrier can be stopped when the first sample reaches the position of the photometric system by stopping said carrier after shifting it for a certain definite distance as measured from its start position so far as the sample are applied at correct positions. Though the intervals may be changed due to construction of the carrier, such change is generally slight and the carrier can be stopped when the center of the first sample reaches almost the position of the photometric system. When the carrier is stopped, the center $y_1$ of the second sample $2'$ apart by a distance of sample interval 1 from the photometric system is located between the ends of 11a, 12a, ... and 21a, 22a, ... of the optical fiber groups 10 and 20 respectively. Further, for the time before the first sample reaches the position of the photometric system, the light emitting diodes 31, 32, ... are glowed consecutively as already described above so as to receive the lights having passed through a portion free from sample of the carrier with the photo detector element 40 and outputs corresponding to intensities of the lights are stored. Let us designates the output data by $V_{a1}, V_{a2}, \ldots V_{a8}$ respectively. These output data are different from one another depending on difference in transmittance of the individual optical fibers, etc. as shown in FIG. 10A. Then a light emitting diode to be utilized for detecting sample is to be selected. At the time when the first sample 2 is located at the position of the photometric system and the second sample $2'$ is located over the optical fibers, the light emitting diodes are glowed consecutively. Let us designates outputs obtained at this time by $V_{b1}, V_{b2}, \ldots V_{b8}$ respectively as illustrated in FIG. 10B. Therefore, outputs $V_{a1}, \ldots$ shown in FIG. 10A and higher outputs $V_{a1}, \ldots$ shown in FIG. 10B correspond to a portion free from sample of the carrier and lower outputs $V_{b1}, \ldots$ shown in FIG. 10B correspond to a sample applied onto the carrier. That is to say, the portions slashed in FIG. 10B represent reduction in light intensities due to concentration of the sample. Reduction ratios of the light intensities $(V_{an}-V_{bn})/V_{an}$ (n=1, 2, ... 8) are calculated to select the light emitting diode corresponding to the highest ratio as the one to be utilized for sample detection. On the example shown in FIG. 10B, for instance, the output corresponding to the fifth light emitting diode represents the highest reduction ratio and the said light emitting diode is selected as the one to be utilized for sample detection.

Then, a sample detection level is to be selected. When the light emitting diode 35, for example, is selected for sample detection, the detection level $V_r$ is determined as follows:

$$V_r = V_{b5} + (V_{a5} - V_{b5}) \times A$$

wherein the reference symbol A represents a setting value at a constant level (for example, 0.5) within a range of $0 < A < 1$.

That is to say, the line A represents the detection level thus determined in FIG. 10B.

After a light emitting diode has been selected and a standard level has been preset as described above, position of sample is to be detected.

Figure 1:
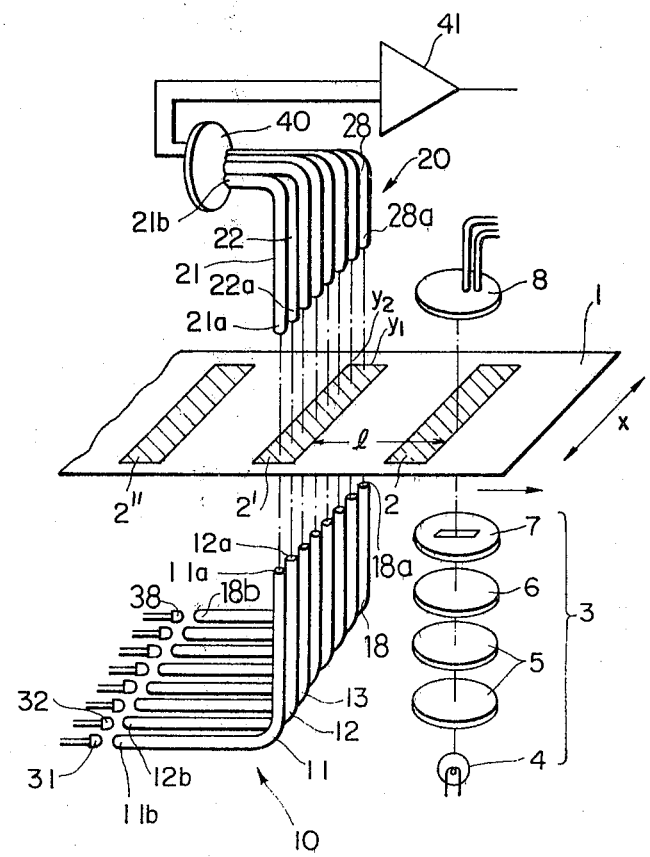
FIG. 1 shows a diagram illustrating construction of a sample detector of the type similar to that used for the method according to the present invention.
Figure 2:
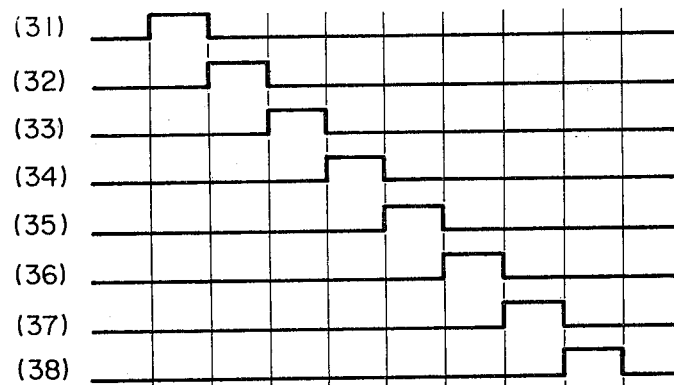
FIG. 2 shows a chart illustrating glowing timing for the light emitting diodes in said sample detector.
Figure 3:
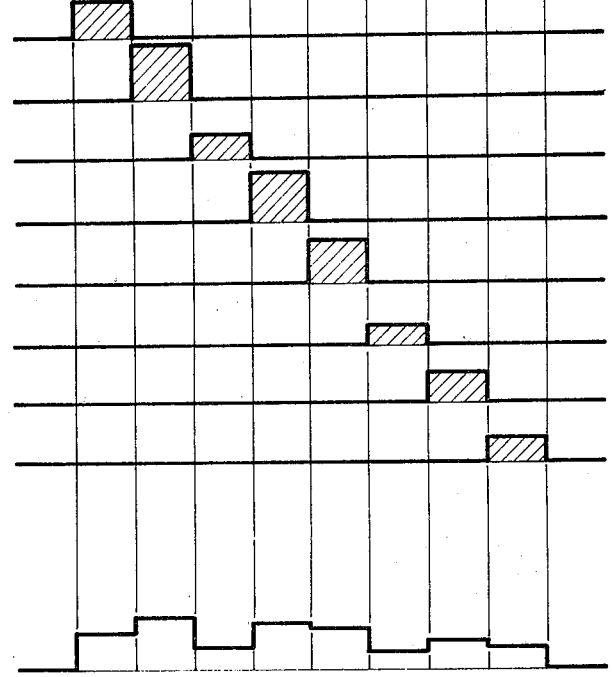
FIG. 3 shows a chart illustrating outputs from a photo detector obtained at the timing illustrated in FIG. 2.
Figure 4:
FIG. 4 shows a chart illustrating total of the outputs shown in FIG. 3.
Figure 7:
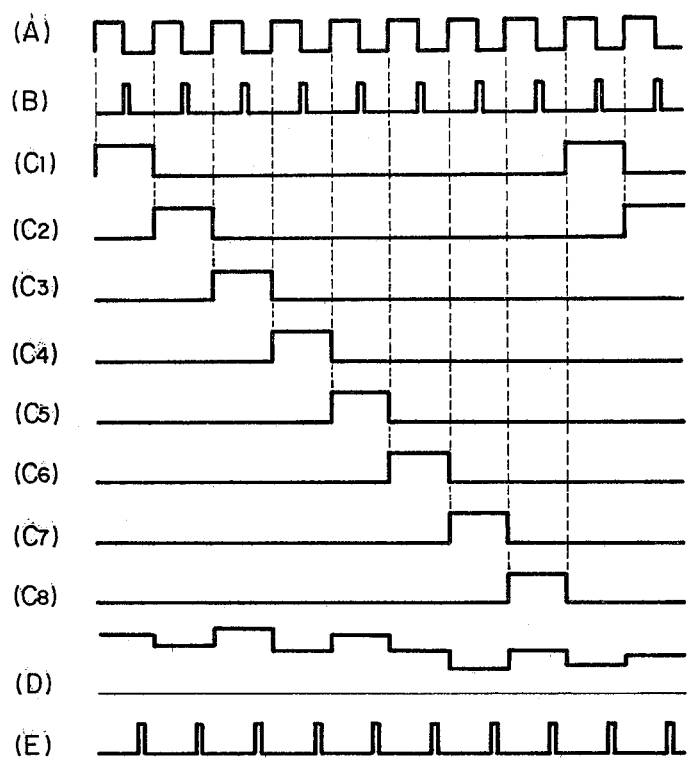
FIG. 7 shows a chart illustrating output signals, etc. at the respective stages of the circuit shown in FIG. 6.
Figure 8:
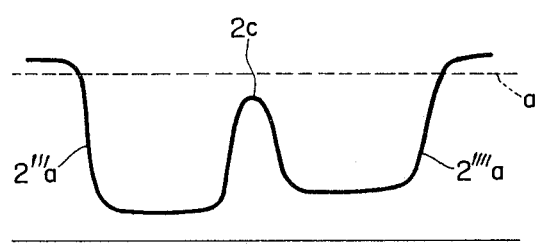
FIG. 8 shows a diagram illustrating an example of outputs corresponding to two neighboring samples.
Figure 9:
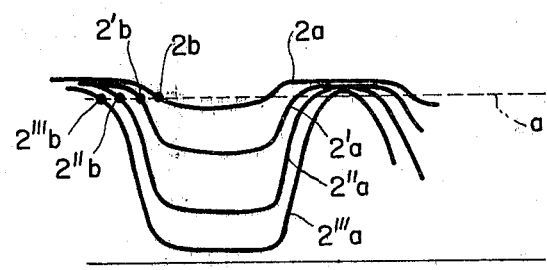
FIG. 9 shows a diagram illustrating difference in outputs depending on difference in concentrations of samples.
Figure 11:
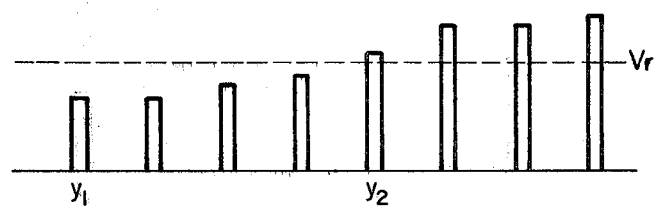
FIG. 11 shows a diagram illustrating an example for detecting end edge of a sample by the method according to the present invention.

At the initial stage, the rows of the optical fibers of both the optical fiber groups are located at the position $y_1$ as shown in FIG. 1. When the carrier is shifted from this position in the direction indicated by the arrow and the light emitting diodes are glowed consecutively, output from the light emitting diode selected for sample detection varies consecutively as illustrated in FIG. 11. While the carrier is being shifted in this way, the optical fiber groups deviate from the sample at the position $y_2$ shown in FIG. 1. Observation of the output from the light emitting diode selected for sample detection at this time permits detecting a change point from an output level lower than the sample detection level (dark level) to another output level higher than the sample detection level (bright level) which corresponds to sample detection time, i.e., end edge of a sample. By stopping the shifting of the carrier at a time when the carrier is shifted in the direction indicated by the arrow for a distance equal to the distance from which the distance between the center of the sample to the position $y_2$ is subtracted, the center of the sample is located at the position of the photometric system.

Therefore, photometry of the sample can be carried out by scanning it in the x direction. At this stopping position, the next sample is located between the ends of the optical fiber groups which are arranged opposite to each other. The end edge of the next sample $2''$ can be detected by carrying out measurements for detecting its position to determine values of $V_{b1}, V_{b2}, \ldots V_{bn}$ by the sample detection method described above. Positions of all the samples can be detected by repeating these procedures.

Though the foregoing descriptions have been given on an embodiment using eight optical fibers for each of the optical fiber groups and eight light emitting diodes composing the sample detector selected as an example, the method according to the present invention is not limited to this embodiment but is compatible with the above-mentioned members arranged in a number sufficient to cover a sample in the x direction. The sample detection method according to the present invention permits glowing all the light emitting diodes consecutively even after a photo detector has been selected for sample detection and using output corresponding only to the light emitting diode for the selected photo detector for detecting sample position, or glowing the light emitting only diode for the selected photo detector at a certain constant time intervals for carrying out sample detection.

As is understood from the foregoing descriptions, the sample detection method according to the present invention makes it possible to carry out stable sample detection even at little difference in concentrations of samples since it selects a sample detector providing the leargest concentration difference between bright level and dark level out of plural number of sample detectors arranged in the direction perpendicular to the shifting direction of the carrier, and eliminate the fear of detecting incapability even at large concentration difference since it permits selecting an adequate level matched with concentration difference as a standard level for sample detection.

We claim:

1. A method for detecting samples comprising a step to detect outputs corresponding to a carrier portion free from sample with a plural number of sample detectors arranged in the direction perpendicular to the shifting direction of a carrier, a step to detect outputs corresponding to a carrier portion onto which a sample is applied with said sample detectors, a step to select a sample detector providing the largest difference between the output corresponding to the carrier portion free from sample and that corresponding to the carrier portion onto which the sample is applied as the detector to be utilized for detecting position of the sample, a step to set a standard level for said sample detector selected for detecting position of the sample and a step to detect the end edge of the sample by determining a time at which output from said sample detector selected for sample detection changes from a level higher than the standard level to another level lower than said standard level.

2. A method for detecting samples according to claim 1 so adapted as to set said standard level as Vr determined by the following equation:

$$V_r = V_{bi} + (V_{ai} - V_{bi}) \times A$$

wherein the reference symbol $V_{ai}$ ($V_{a1}$, $V_{a2}$, ... $V_{an}$) represents outputs of the individual sample detectors obtained at the step to detect outputs corresponding to said carrier portion free from sample, the reference symbol $V_{bi}$ ($V_{b1}$, $V_{b2}$, ... $V_{bn}$) designates outputs of the individual sample detectors obtained at the step to detect outputs corresponding to the carrier portion onto which a sample is applied, and the reference symbol A denotes a value optionally selectable within a range of $0 < A < 1$.

* * * * *